US012751741B2

(12) United States Patent
Oikawa et al.

(10) Patent No.: US 12,751,741 B2
(45) Date of Patent: *Oct. 6, 2026

(54) ROD FOR SPINAL FIXATION IMPLEMENT AND SPINAL FIXATION IMPLEMENT PROVIDED WITH SAME

(71) Applicant: GLOBERIDE, Inc., Tokyo (JP)

(72) Inventors: Katsuhiro Oikawa, Tokyo (JP); Takuji Kawamura, Tokyo (JP)

(73) Assignee: GLOBERIDE, Inc., Tokyo (JP)

( * ) Notice: Subject to any disclaimer, the term of this patent is extended or adjusted under 35 U.S.C. 154(b) by 180 days.

This patent is subject to a terminal disclaimer.

(21) Appl. No.: 18/272,981

(22) PCT Filed: Oct. 12, 2021

(86) PCT No.: PCT/JP2021/037721
§ 371 (c)(1),
(2) Date: Jul. 18, 2023

(87) PCT Pub. No.: WO2022/158058
PCT Pub. Date: Jul. 28, 2022

(65) Prior Publication Data

US 2024/0081867 A1 Mar. 14, 2024

(30) Foreign Application Priority Data

Jan. 25, 2021 (JP) ................................ 2021-009692

(51) Int. Cl.
*A61B 17/70* (2006.01)
*A61L 31/10* (2006.01)
(Continued)

(52) U.S. Cl.
CPC .......... *A61B 17/7002* (2013.01); *A61L 31/10* (2013.01); *A61L 31/125* (2013.01);
(Continued)

(58) Field of Classification Search
CPC .................................. A61B 17/7002–17/7013
See application file for complete search history.

(56) References Cited

U.S. PATENT DOCUMENTS 5,415,661 A 5/1995 Holmes
5,556,687 A 9/1996 McMillin
(Continued)

FOREIGN PATENT DOCUMENTS

DE 102013013024 A1 * 2/2014 ......... A61B 17/7004
EP 2 389 124 A0 11/2011
(Continued)

OTHER PUBLICATIONS

International Preliminary Report on Patentability for related International Application No. PCT/JP2021/037721; action dated Jul. 20, 2023; (12 pages).
(Continued)

*Primary Examiner* — Julianna N Harvey
(74) *Attorney, Agent, or Firm* — Oliff PLC

(57) ABSTRACT

Provided is a fixture rod that is excellent in bonding strength between a core material and a reinforcing fiber layer and has high rigidity and high durability against a deformation load. A fixture rod according to one embodiment of the present disclosure comprises: a core member containing a resin; and a reinforcing fiber layer provided on the core member, and is configured such that the resin of the core member and a resin of the reinforcing fiber layer are the same resin, or the resin of the core member and the resin of the reinforcing fiber layer are different resins, and a critical surface tension of each of the resin of the core member and the resin of the reinforcing fiber layer is 20 mN/m or more.

13 Claims, 8 Drawing Sheets

(51) Int. Cl.

| | |
|---|---|
| ***A61L 31/12*** | (2006.01) |
| ***A61L 31/14*** | (2006.01) |
| ***B29C 70/08*** | (2006.01) |
| *B29C 70/54* | (2006.01) |
| *B29L 31/00* | (2006.01) |

(52) U.S. Cl.

CPC ............ *A61L 31/143* (2013.01); *B29C 70/08* (2013.01); *B29C 70/545* (2013.01); *B29K 2995/0094* (2013.01); *B29L 2031/753* (2013.01)

(56) References Cited

U.S. PATENT DOCUMENTS

| | | | | |
|---|---|---|---|---|
| 2004/0049189 | A1 | 3/2004 | Le Couedic et al. | |
| 2004/0215191 | A1 | 10/2004 | Kitchen | |
| 2006/0189982 | A1 * | 8/2006 | Lange | A61B 17/701 606/301 |
| 2006/0247638 | A1 | 11/2006 | Trieu et al. | |
| 2006/0276788 | A1 * | 12/2006 | Berry | A61B 17/7005 606/301 |
| 2007/0233073 | A1 | 10/2007 | Wisnewski et al. | |
| 2008/0177317 | A1 | 7/2008 | Jackson | |
| 2008/0234744 | A1 * | 9/2008 | Zylber | A61B 17/7022 606/264 |
| 2008/0262548 | A1 | 10/2008 | Lange et al. | |
| 2009/0018583 | A1 | 1/2009 | Song et al. | |
| 2009/0093819 | A1 | 4/2009 | Joshi | |
| 2009/0112265 | A1 | 4/2009 | Hudgins et al. | |
| 2009/0118831 | A1 | 5/2009 | Trieu | |
| 2009/0163955 | A1 | 6/2009 | Moumene et al. | |
| 2009/0281573 | A1 | 11/2009 | Biedermann et al. | |
| 2009/0287251 | A1 | 11/2009 | Bae et al. | |
| 2010/0137912 | A1 | 6/2010 | Alcock et al. | |
| 2011/0060365 | A1 | 3/2011 | Felix et al. | |
| 2011/0071570 | A1 | 3/2011 | Trieu | |
| 2011/0106162 | A1 * | 5/2011 | Ballard | A61B 17/701 606/279 |
| 2011/0152937 | A1 | 6/2011 | Trieu | |
| 2011/0282395 | A1 | 11/2011 | Beyar et al. | |
| 2011/0307014 | A1 | 12/2011 | Niinomi et al. | |
| 2012/0029564 | A1 | 2/2012 | Trieu et al. | |
| 2012/0071928 | A1 | 3/2012 | Jackson | |
| 2012/0196068 | A1 | 8/2012 | Gong et al. | |
| 2013/0204368 | A1 | 8/2013 | Prevost | |
| 2013/0213535 | A1 | 8/2013 | Niinomi et al. | |
| 2015/0209095 | A1 * | 7/2015 | Lu | A61L 31/028 424/602 |
| 2016/0303824 | A1 * | 10/2016 | Takebe | B29C 70/0035 |
| 2017/0042593 | A1 | 2/2017 | Newman et al. | |
| 2024/0058038 | A1 | 2/2024 | Oikawa et al. | |

FOREIGN PATENT DOCUMENTS

| | | | |
|---|---|---|---|
| EP | 2 982 504 | A1 | 2/2016 |
| EP | 3236866 | A1 | 11/2017 |
| GB | 2256615 | A | 12/1992 |
| JP | H04366616 | A | 12/1992 |
| JP | H11296033 | A | 10/1999 |
| JP | H11347047 | A | 12/1999 |
| JP | 2011508623 | A | 3/2011 |
| JP | 2011256443 | A | 12/2011 |
| JP | 2015-186641 | A | 10/2015 |
| JP | 2020-137454 | A | 9/2020 |
| KR | 102187523 | B1 | 12/2020 |
| WO | 2006/044315 | A2 | 4/2006 |
| WO | 2007/097905 | A2 | 8/2007 |
| WO | 2011042998 | A1 | 4/2011 |
| WO | 2014162873 | A1 | 10/2014 |

OTHER PUBLICATIONS

Dec. 5, 2023 Office Action issued in Japanese Patent Application No. 2021-009692.

Jul. 31, 2024 Extended European Search Report issued in European Patent Application No. 21921161.2.

International Search Report for related International Application No. PCT/JP2021/037721; action dated Jul. 28, 2022; (3 pages).

Written Opinion for related International Application No. PCT/JP2021/037721; action dated Jul. 28, 2022; (5 pages).

Jul. 2, 2024 Extended European Search Report issued in European Patent Application No. 21917551.0.

Mar. 31, 2025 Office Action issued in U.S. Appl. No. 18/269,488.

Jul. 4, 2023 International Preliminary Report issued in International Patent Application No. PCT/JP2021/037720.

Jul. 14, 2022 International Search Report issued in International Patent Application No. PCT/JP2021/037720.

Jul. 14, 2022 Written Opinion issued in International Patent Application No. PCT/JP2021/037720.

May 20, 2025 Office Action issued in Korean Patent Application No. 10-2023-7023502.

Dec. 5, 2023 Office Action issued in Japanese Patent Application No. 2021-000613.

Jul. 15, 2025 Office Action issued in Korean Patent Application No. 10-2023-7028508.

Aug. 11, 2025 Office Action issued in U.S. Appl. No. 18/027,818.

Feb. 28, 2025 Office Action issued in U.S. Appl. No. 18/027,818.

Jun. 19, 2025 Office Action issued in Chinese Patent Application No. 202180053600.2.

Feb. 19, 2025 Office Action issued in Korean Patent Application No. 10-2023-7006589.

Dec. 11, 2024 Office Action issued in Chinese Patent Application No. 202180053600.2.

Apr. 26, 2024 Search Report issued in European Patent Application No. 21875136.0.

Nov. 21, 2023 Office Action issued in Japanese Patent Application No. 2020-163964.

Olffice Action for related Japanese Application No. 2020-163964; action dated Jun. 27, 2023; (7 pages).

Preliminary Report on Patentability for related International Application No. PCT/JP2021/033268; action dated Mar. 28, 2023; (9 pages).

International Search Report for related International Application No. PCT/JP2021/033268; action dated Apr. 7, 2022; 5 pages).

Written Opinion for related International Application No. PCT/JP2021/033268; action dated Apr. 7, 2022; (4 pages).

Sep. 27, 2025 Office Action issued in Chinese Patent Application No. 202180088813.9.

Aug. 11, 2025 Office Action issued in U.S. Appl. No. 18/269,488.

May 6, 2026 Notice of Allowance issued in U.S. Appl. No. 18/269,488.

Dec. 25, 2025 Office Action issued in Chinese Patent Application No. 202180091658.6.

Jan. 15, 2026 Office Action issued in U.S. Appl. No. 18/269,488.

Feb. 7, 2026 Office Action issued in Chinese Patent Application No. 202180088813.9.

May 10, 2026 Office Action issued in Chinese Patent Application No. 202180091658.6.

Jun. 24, 2026 Office Action issued in Chinese Patent Application No. 202180088813.9.

May 29, 2026 Office Action issued in Korean Patent Application No. 10-2023-7028508.

* cited by examiner

ROD FOR SPINAL FIXATION IMPLEMENT AND SPINAL FIXATION IMPLEMENT PROVIDED WITH SAME

CROSS-REFERENCE TO RELATED APPLICATIONS

The present application is a National Stage of International Application No. PCT/JP2021/037721 filed on Oct. 12, 2021 which claims priority to and the benefit of Japanese Patent Application No. 2021-009692 filed on Jan. 25, 2021, the contents of which are incorporated herein by reference in their entirety.

FIELD

The present disclosure relates to a fixture rod used for a fixture configured to fix a spine and a spinal fixture comprising the same.

BACKGROUND

Conventionally, a fixture rod using metal as a fixture for fixing the spine has been known.

Further, as such a fixture rod, for example, Patent Literature 1 discloses a spinal pedicle rod comprising an internally reinforced polymer core at least partially encased in a polymer coating.

CITATION LIST

Patent Literature

Patent Literature 1: Japanese Translation of PCT International Application Publication No. 2011-508623

SUMMARY

A fixture rod using metal is generally excellent in fixing force and strength, but has a problem that a magnetic field is affected by magnetization of the metal in the magnetic field at the time of imaging by MRI or the like, image disturbance occurs, and diagnosis based on a captured image is difficult. On the other hand, the rod disclosed in Patent Literature 1 does not have such a problem, but has a problem that it is difficult to reliably achieve uniform bonding even if an adhesive is used for bonding between a polymer core material and a covering layer thereof, and it is difficult to obtain stable bonding strength.

An object of the present disclosure is to provide a fixture rod that is excellent in bonding strength between a core material and a reinforcing fiber layer and has high rigidity and high durability against a deformation load, and a spinal fixture comprising the same. Purposes of the present disclosure other than this object will be clarified by referring to the overall description disclosed herein.

A fixture rod according to one embodiment of the present disclosure comprises: a core member containing a resin; and a reinforcing fiber layer provided on the core member, and is configured such that the resin of the core member and a resin of the reinforcing fiber layer are the same resin, or the resin of the core member and the resin of the reinforcing fiber layer are different resins, and a critical surface tension of each of the resin of the core member and the resin of the reinforcing fiber layer is 20 mN/m or more.

In the fixture rod according to one embodiment of the present disclosure, one recess or a plurality of recesses are formed on an outer surface of the core member.

In the fixture rod according to one embodiment of the present disclosure, the recess is formed in a circumferential direction of the core member.

In the fixture rod according to one embodiment of the present disclosure, the recess is formed in an axial direction of the core member.

In the fixture rod according to one embodiment of the present disclosure, the recess is formed in a direction inclined with respect to a circumferential direction of the core member.

In the fixture rod according to one embodiment of the present disclosure, the recesses comprise two or more recesses formed in different directions.

In the fixture rod according to one embodiment of the present disclosure, a depth of the recess is in a range of 3 μm to 200 μm.

In the fixture rod according to one embodiment of the present disclosure, the core member is formed using the resin containing a fiber.

In the fixture rod according to one embodiment of the present disclosure, the fiber of the core member is partially exposed from the core member.

In the fixture rod according to one embodiment of the present disclosure, the fiber of the core member is a long fiber. Further, in the fixture rod according to one embodiment of the present disclosure, the fiber of the core member is a short fiber.

The fixture rod according to one embodiment of the present disclosure is configured such that the resin of the core member is any of epoxy, phenol, unsaturated polyester, PA, PC, PPSU, POM, PP, PE, ABS, PS, PAEK, or PEEK.

A spinal fixture according to one embodiment of the present disclosure comprises any of the fixture rods described above.

According to each of the above embodiments of the present disclosure, it is possible to provide the fixture rod that is excellent in bonding strength between the core material and the reinforcing fiber layer and has high rigidity and high durability against the deformation load, and the spinal fixture comprising the same.

FIG. **3*a*** is a view for describing a core member of the fixture rod according to one embodiment of the present disclosure.

FIG. **3*b*** is a view for describing a core member of the fixture rod according to one embodiment of the present disclosure.

FIG. **4*a*** is a view for describing a core member of the fixture rod according to one embodiment of the present disclosure.

FIG. **4*b*** is a view for describing a core member of the fixture rod according to one embodiment of the present disclosure.

Figure 5:
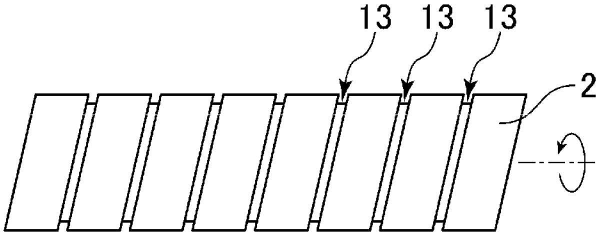

FIG. 5 is a view for describing a core member of the fixture rod according to one embodiment of the present disclosure.

Figure 6:
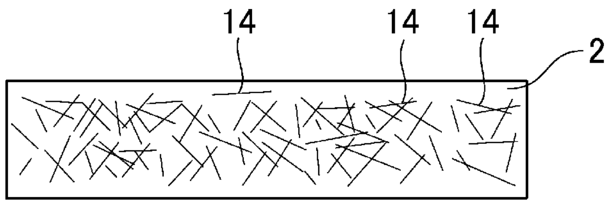

FIG. 6 is a view for describing a core member of the fixture rod according to one embodiment of the present disclosure.

Figure 7A:
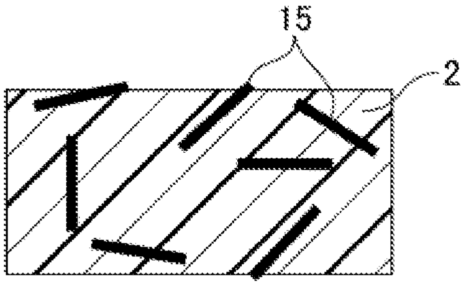
Figure 7B:
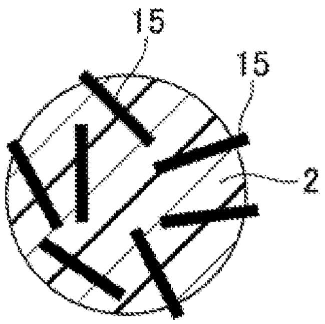

FIG. 7 is a view for describing a core member of the fixture rod according to one embodiment of the present disclosure.

Figure 8A:
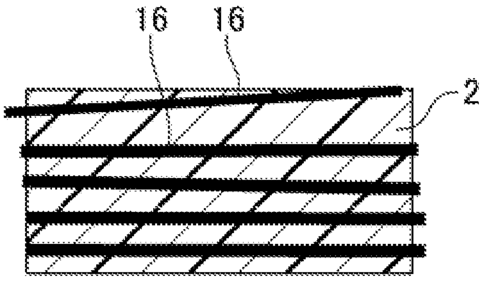
Figure 8B:
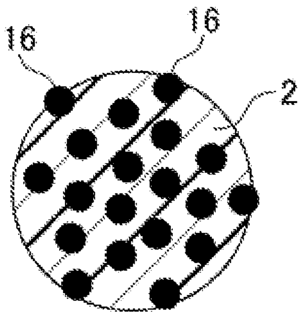

FIG. 8 is a view for describing a core member of the fixture rod according to one embodiment of the present disclosure.

Figure 9A:
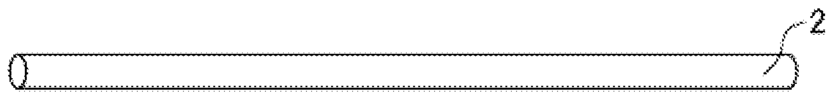

FIG. 9*a* is a view for describing a method for molding the fixture rod according to one embodiment of the present disclosure.

Figure 9B:
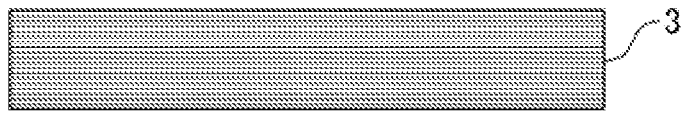

FIG. 9*b* is a view for describing a method for molding the fixture rod according to one embodiment of the present disclosure.

Figure 9C:
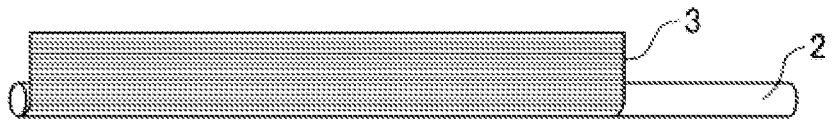

FIG. 9*c* is a view for describing a method for molding the fixture rod according to one embodiment of the present disclosure.

Figure 9D:
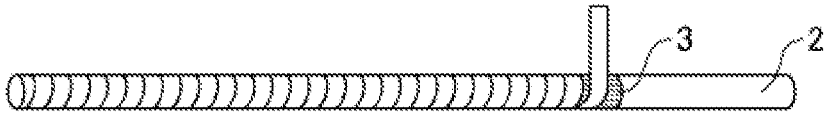

FIG. 9*d* is a view for describing a method for molding the fixture rod according to one embodiment of the present disclosure.

Figure 9E:
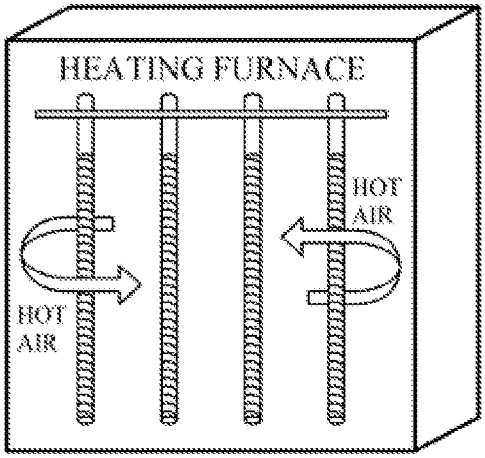

FIG. 9*e* is a view for describing a method for molding the fixture rod according to one embodiment of the present disclosure.

Figure 9F:
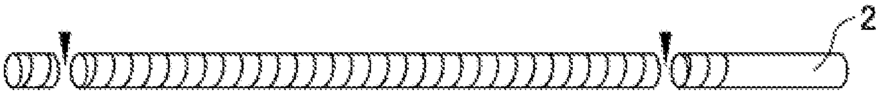

FIG. 9*f* is a view for describing a method for molding the fixture rod according to one embodiment of the present disclosure.

Figure 9G:
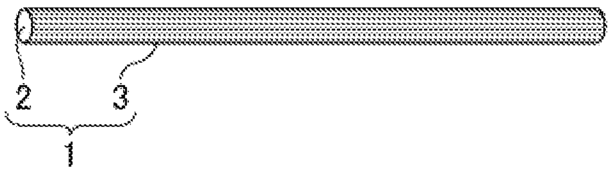

FIG. 9*g* is a view for describing a method for molding the fixture rod according to one embodiment of the present disclosure.

DETAILED DESCRIPTION

Hereinafter, an embodiment of a fixture rod according to the present disclosure will be specifically described with reference to the accompanying drawings. Components common in a plurality of drawings are assigned with the same reference signs throughout the plurality of drawings. It should be noted that each of the drawings is not always illustrated in a precise aspect ratio for the convenience of description.

Figure 1:
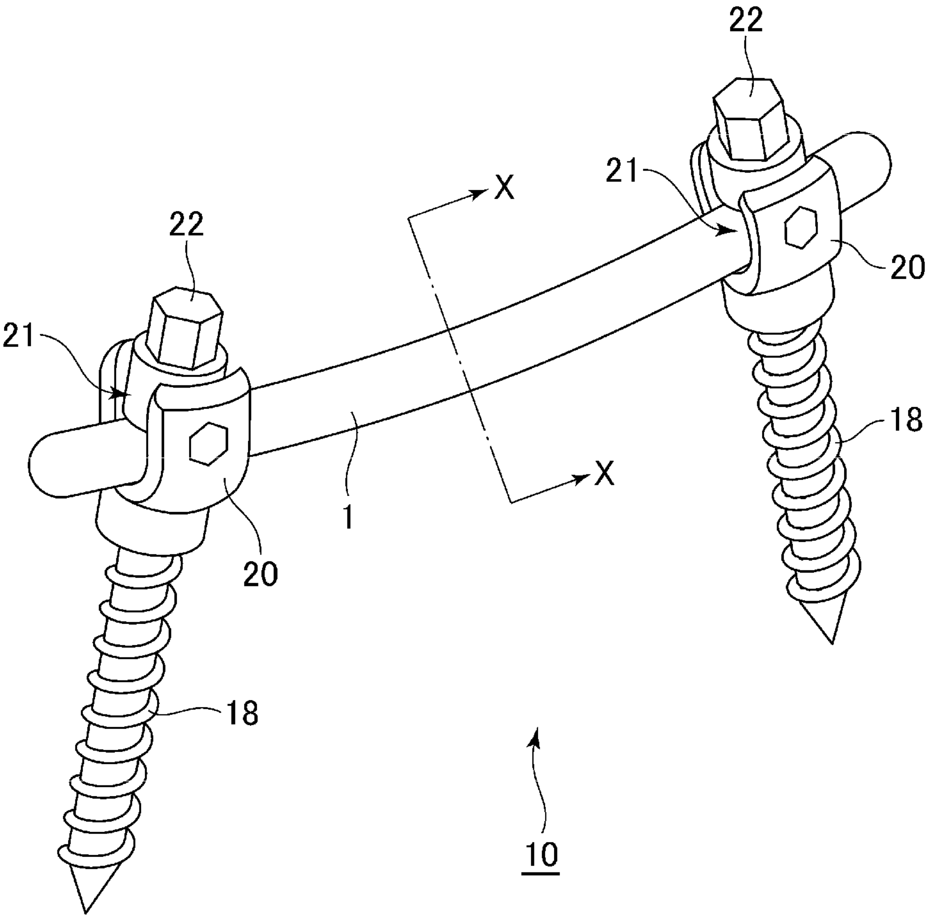
FIG. 1 is a view illustrating a spinal fixture 10 comprising a fixture rod according to one embodiment of the present disclosure.

FIG. 1 is a view illustrating a spinal fixture 10 comprising a fixture rod 1 according to one embodiment of the present disclosure. As illustrated in the drawing, the spinal fixture 10 comprises a plurality of screw members 18 (two screw members 18 in the example illustrated in the drawing) to be fixed to the bone of the spine, a plurality of rod fixing members 20 (two rod fixing members 20 in the example illustrated in the drawing) attached to the screw members 18 and each comprising a recess 21 for receiving the fixture rod and a pressing member 22, and the fixture rod 1 inserted into the recess 21 of the plurality of rod fixing members 20 and fixed by the pressing member 22.

Figure 2:
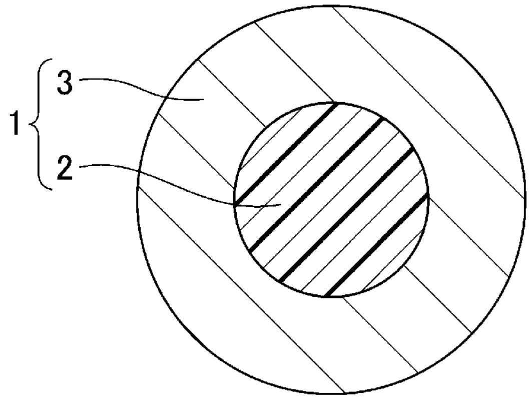
FIG. 2 is a view schematically illustrating a cross section of the fixture rod according to one embodiment of the present disclosure taken along a plane perpendicular to a central axis thereof.

Next, the fixture rod 1 according to one embodiment of the present disclosure used for the spinal fixture 10 will be described with reference to FIG. 2. FIG. 2 illustrates the fixture rod 1 illustrated in FIG. 1 as viewed in X-X section illustrated in the same drawing.

As illustrated in the drawing, the fixture rod 1 according to one embodiment of the present disclosure comprises: a core member 2 containing a resin; and a reinforcing fiber layer 3 provided on the core member 2, and is configured such that the resin of the core member 2 and a resin of the reinforcing fiber layer 3 are the same resin, or the resin of the core member and the resin of the reinforcing fiber layer are different resins, and a critical surface tension of each of the resin of the core member and the resin of the reinforcing fiber layer is 20 mN/m or more.

According to the fixture rod 1 according to one embodiment of the present disclosure, it is possible to provide the fixture rod that is excellent in bonding strength between a core material and the reinforcing fiber layer and has high rigidity and high durability against a deformation load. More specifically, the affinity between the core material and the reinforcing fiber layer is improved, and the bonding strength between the core material and the reinforcing fiber layer is excellent when the resin of the core member and the resin of the reinforcing fiber layer each having the critical surface tension of 20 mN/m or more are adopted whether the same resin or different resins are used, Further, a solid double structure is adopted, and a material having a large average bending elastic modulus is used for an outer layer as will be described later, and thus, it is possible to provide the fixture rod having excellent bending rigidity and crushing strength of the entire rod. Here, the average bending elastic modulus refers to a value calculated by dividing the bending rigidity of the entire corresponding portion by a second moment of the corresponding portion.

Here, even if the resin of the core member and the resin of the reinforcing fiber layer are different resins, it has been confirmed that the critical surface tension of the resin exceeds desired bonding performance in bonding between different types of materials when the critical surface tensions of the resin of the core member and the resin of the reinforcing fiber layer are 20 mN/m or more, and it has been found that a special process, such as a chemical solution treatment or a plasma treatment, for bonding is unnecessary. More specifically, for example, critical surface tensions of polypropylene (PP), polyethylene (PE), polystyrene (PS), polyoxymethylene (POM), polyethylene terephthalate (PET), and nylon 66 are 22 to 29 mN/m, 31 mN/m, 33 mN/m, 36 to 38 mN/m, 43 mN/m, and 46 mN/m, respectively, and it has been found that favorable bonding performance is exhibited due to the critical surface tensions of the resins even if the resin of the core member and the resin of the reinforcing fiber layer are different resins. On the other hand, a critical surface tension of polytetrafluoroethylene paraffin (PTFE) is 18.5 mN/m, and it has been found that a special process, such as a chemical liquid treatment or a plasma treatment, for bonding is required because the critical surface tension of the resin is lower than the desired bonding performance in bonding between different types of materials. However, this is not applied when the resin of the core member and the resin of the reinforcing fiber layer are the same resin.

In the fixture rod 1 according to one embodiment of the present disclosure, a thermosetting resin (for example, epoxy, phenol, unsaturated polyester, or the like) or a thermoplastic resin (for example, PA, PC, PPSU, POM, PP, PE, ABS, PS, PAEK, PEEK, or the like) is used as the resin of the core member 2.

In the fixture rod 1 according to one embodiment of the present disclosure, the core member 2 can be formed using a resin containing fibers. In such a case, it is configured such that the fiber is any of carbon, glass, aramid, boron, or SiC, and the resin is a thermosetting resin (for example, epoxy, phenol, unsaturated polyester, or the like) or a thermoplastic resin (for example, PA, PC, PPSU, POM, PP, PE, ABS, PS, PAEK, PEEK, or the like). With this configuration, it is possible to increase the bending rigidity and the strength of the core member.

In the fixture rod 1 according to one embodiment of the present disclosure, the reinforcing fiber layer 3 is a fiber-reinforced resin, carbon, glass, boron, SiC, or aramid is used as a fiber, and a thermosetting resin (for example, epoxy, phenol, unsaturated polyester, or the like) or a thermoplastic resin (for example, PA, PC, PPSU, POM, PP, PE, ABS, PS, PAEK, PEEK, or the like) is used as a resin. With this configuration, it is possible to increase the bending rigidity and the strength of the reinforcing fiber layer.

It is configured such that the fixture rod 1 according to one embodiment of the present disclosure comprises a covering layer provided on the reinforcing fiber layer 3. The covering layer can be formed using, for example, epoxy, phenol, unsaturated polyester, PA, PC, PPSU, POM, PP, PE, ABS, PS, PAEK, or PEEK, but is not limited thereto.

Next, the core member 2 of the fixture rod 1 according to one embodiment of the present disclosure used for the spinal fixture 10 will be described with reference to FIGS. 3 to 8. In the fixture rod 1 according to one embodiment of the present disclosure, one or a plurality of recesses are formed on an outer surface of the core member 2. As a result, the contact surface area between the core member 2 and the reinforcing fiber layer 3 increases during molding, so that the bonding strength between the core material and the reinforcing fiber layer can be significantly improved. This will be described more specifically below.

Figure 3:
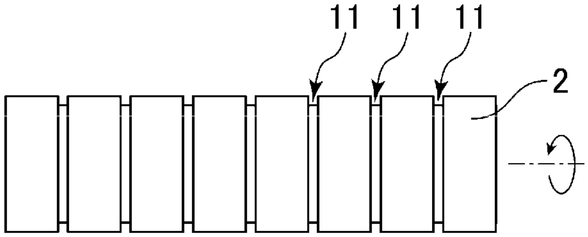

As illustrated in FIG. 3, recesses (circumferential recesses) 11 are formed in a circumferential direction of the core member 2 in the fixture rod 1 according to one embodiment of the present disclosure. Although seven recesses 11 are formed in the example illustrated in the drawing, any desired number of recesses can be provided, and the number is not limited to a specific number. Further, the recess 11 can be formed in the whole or a part of the core member 2 in the circumferential direction Alternatively, the recess 11 may be intermittently formed in the whole or a part of the core member 2 in the circumferential direction. When the recess is provided in the circumferential direction of the core member in this manner, the bonding area increases, and axial displacement between the core member 2 and the reinforcing fiber layer 3 can be suppressed.

Figure 4:
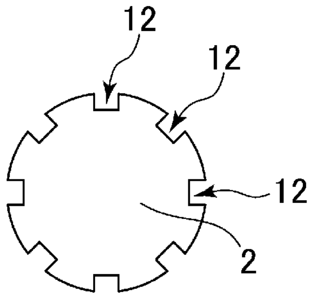

Next, as illustrated in FIG. 4, recesses (axial recesses) 12 are formed in an axial direction of the core member 2 in the fixture rod 1 according to one embodiment of the present disclosure. Although eight recesses 12 are formed in the example illustrated in the drawing, any desired number of recesses can be provided, and the number is not limited to a specific number. Further, the recess 12 can be formed in the whole or a part of the core member 2 in the axial direction Alternatively, the recess 12 may be intermittently formed in the whole or a part of the core member 2 in the axial direction. When the recess is provided in the axial direction of the core member in this manner, the bonding area increases, and rotational displacement between the core member 2 and the reinforcing fiber layer 3 can be suppressed.

Next, as illustrated in FIG. 5, recesses (inclined-direction recesses) 13 are formed so as to be inclined with respect to the circumferential direction of the core member 2 in the fixture rod 1 according to one embodiment of the present disclosure. Although seven recesses 13 are formed in the example illustrated in the drawing, any desired number of recesses can be provided, and the number is not limited to a specific number. Further, the recess 13 can be formed on the whole or a part of the circumference of the core member 2. Alternatively, the recess 13 may be intermittently formed on the whole or a part of the circumference of the core member 2. When the recess is provided in a direction inclined with respect to the circumferential direction of the core member in this manner, the bonding area increases, and the axial displacement and rotational displacement between the core member 2 and the reinforcing fiber layer 3 can be suppressed.

Next, as illustrated in FIG. 6, recesses (different-direction recesses) 14 are formed on the surface of the core member 2 so as to comprise two or more recesses formed in different directions in the fixture rod 1 according to one embodiment of the present disclosure. Although many recesses 14 are formed in the example illustrated in the drawing, any desired number of recesses can be provided, and the number is not limited to a specific number. Further, in a case where there are three or more recesses 14, two or more recesses 14 thereof may be formed in the same direction. Further, the recesses 14 can be formed on the whole or a part of the surface of the core member 2. Alternatively, the recess 11 may be intermittently formed on the whole or a part of the surface of the core member 2. When the recesses are provided in different directions in this manner, it is possible to suppress displacement in a plurality of different directions.

In the fixture rod according to one embodiment of the present disclosure, a depth of the recess is in a range of 3 μm to 200 μm. As a result, it is possible to set an appropriate range in which the displacement between the core member 2 and the reinforcing fiber layer 3 is suppressed while suppressing a change and a variation in the rigidity due to the recess.

In the fixture rod 1 according to one embodiment of the present disclosure, the core member 2 can be formed using a resin containing fibers, and is configured such that the fibers of the core member are short fibers. When the short fibers are used, fiber directions can be randomly oriented, and reinforcement in all directions is possible.

In the fixture rod 1 according to one embodiment of the present disclosure, the core member 2 can be formed using a resin containing fibers, and is configured such that the fibers of the core member are long fibers. As a result, the bending rigidity can be effectively improved.

Next, as described above, the core member 2 can be formed using a resin containing fibers in the fixture rod 1 according to one embodiment of the present disclosure. In such a case, as illustrated in FIG. 7, fibers (short fibers) 15 of the core member 2 are partially exposed from the surface of the core member in the fixture rod 1 according to one embodiment of the present disclosure. When the short fibers 15 are exposed in this manner, minute irregularities are generated on the surface of the core member 2, so that the displacement between the core member 2 and the reinforcing fiber layer 3 can be suppressed.

Next, as described above, the core member 2 can be formed using a resin containing fibers in the fixture rod 1 according to one embodiment of the present disclosure. In such a case, as illustrated in FIG. 8, fibers (long fibers) 16 of the core member 2 are partially exposed from the surface of the core member 2 in the fixture rod 1 according to one embodiment of the present disclosure. When the long fibers 16 are exposed in this manner, minute irregularities are generated on the surface of the core member 2, so that the displacement between the core member 2 and the reinforcing fiber layer 3 can be suppressed.

The fixture rod 1 according to one embodiment of the present disclosure is configured such that fibers of the reinforcing fiber layer 3 are long fibers. Since the fibers of the reinforcing fiber layer 3 are long fibers, it is possible to further increase the bending rigidity and the strength.

Further, the fixture rod 1 according to one embodiment of the present disclosure is configured such that a fiber content of one or more layers included in the reinforcing fiber layer 3 is 60% by weight or more. It is possible to form the fixture rod 1 having high rigidity and excellent durability with the fiber layer in which the long fibers are filled at high density in this manner.

Next, a method for manufacturing the fixture rod 1 according to one embodiment of the present disclosure will be described with reference to FIG. 9. First, as Step 1, a core member (core material) (including each of modes in FIGS. 3 to 8 described above) is prepared (FIG. 9*a*). Next, as Step 2, a fiber-reinforced resin material is prepared (FIG. 9*b*). Next, as Step 3, the fiber-reinforced resin material is wound around the core material to form a fiber-reinforced resin material integrated member (FIG. 9*c*).

Next, in Step 4, a tape is wound around an outer surface of a fiber-reinforced resin material integrated member as an outer die (FIG. 9*d*). Next, in Step 5, the fiber-reinforced resin material integrated member around which the tape is wound is fired (molded) (FIG. 9*e*). Thereafter, as Step 6, the fiber-reinforced resin material integrated member after firing is taken out, and an unnecessary portion is cut (FIG. 9*f*). Finally, as Step 7, the tape of the fiber-reinforced resin material integrated member from which the unnecessary portion has been cut is removed, whereby the fixture rod 1 according to one embodiment of the present disclosure comprising the core member and a fiber-reinforced resin layer can be obtained (FIG. 9*g*).

With the fixture rod 1 according to one embodiment of the present disclosure formed in this manner, it is possible to provide the fixture rod that is excellent in bonding strength between the core material and a reinforcing fiber layer and has high rigidity and high durability against a deformation load. More specifically, the affinity between the core material and the reinforcing fiber layer is improved, and the bonding strength between the core material and the reinforcing fiber layer is excellent when the resin of the core member and the resin of the reinforcing fiber layer each having the critical surface tension of 20 mN/m or more are adopted whether the same resin or different resins are used. Further, a solid double structure is adopted, and a material having a large average bending elastic modulus is used for an outer layer as will be described later, and thus, it is possible to provide the fixture rod having excellent bending rigidity and crushing strength of the entire rod. Here, the average bending elastic modulus refers to a value calculated by dividing the bending rigidity of the entire corresponding portion by a second moment of the corresponding portion.

The spinal fixture 10 according to one embodiment of the present disclosure comprises any of the fixture rods 1 described above.

Dimensions, materials, and arrangements of the components described in this specification are not limited to those explicitly described in the embodiments, and the components may be modified to have any dimensions, materials, and arrangements that may fall within the scope of the present disclosure. Further, components not explicitly described herein can be added to the described embodiments, or some of the components described in each embodiment can be omitted.

REFERENCE SIGNS LIST

1 Fixture rod
2 Core member
3 Reinforcing fiber layer
10 Spinal fixture
11 Recess (circumferential recess)
12 Recess (axial recess)
13 Recess (inclined-direction recess)
14 Recesses (different-direction recesses)
15 Fiber (short fiber)
16 Fiber (long fiber)
18 Screw member
20 Rod fixing member
21 Recess
22 Pressing member

The invention claimed is:

1. A fixture rod comprising:

a core member containing a resin, the core member having a plurality of recesses formed on an outer surface of the core member that each have a longest dimension extending in a circumferential direction of the core member or an inclined direction relative to the circumferential direction of the core member, and a depth of each of the plurality of recesses is in a range of from 3 μm to 200 μm; and a reinforcing fiber layer provided on the core member, wherein the resin of the core member and a resin of the reinforcing fiber layer are an identical resin, or the resin of the core member and the resin of the reinforcing fiber layer are different resins, and a critical surface tension of each of the resin of the core member and the resin of the reinforcing fiber layer is 20 mN/m or more.

2. The fixture rod according to claim 1, wherein each of the plurality of recesses is elongate and the longest dimension extends in the circumferential direction of the core member.

3. The fixture rod according to claim 1, wherein each of the plurality of recesses is elongate and the longest dimension extends in the inclined direction relative to the circumferential direction of the core member.

4. The fixture rod according to claim 1, wherein each of the plurality of recesses is elongate, and the longest dimension of two or more recesses of the plurality of recesses extends in different directions.

5. The fixture rod according to claim 1, wherein the core member is formed using the resin containing fibers.

6. The fixture rod according to claim 5, wherein the fibers of the core member comprise fibers partially exposed from the core member.

7. The fixture rod according to claim 5, wherein the fibers of the core member are long fibers.

8. The fixture rod according to claim 5, wherein the fibers of the core member are short fibers.

9. The fixture rod according to claim 1, wherein the resin of the core member is any of epoxy, phenol, unsaturated polyester, PA, PC, PPSU, POM, PP, PE, ABS, PS, PAEK, or PEEK.

10. The fixture rod according to claim 1, wherein each of the plurality of recesses is elongate.

11. The fixture rod according to claim 1, wherein the longest dimension of each of the plurality of recesses extends around the entire circumference of the core member.

12. The fixture rod according to claim 1, wherein, along an axial direction of the core member, the outer surface of the core member alternates between areas where the recess are formed and areas where the recess are not formed.

13. A spinal fixture that is configured to be fixed to a spine and comprises the fixture rod according to claim 1 and a screw.

* * * * *